United States Patent [19]

McBrearty et al.

[11] Patent Number: 5,469,372

[45] Date of Patent: Nov. 21, 1995

[54] OXYGEN CONCENTRATOR REMOTE MONITORING APPARATUS

[75] Inventors: Raymond A. McBrearty, 842 Barnsdale Rd., Allentown, Pa. 18103; William R. Haller, Bethlehem, Pa.

[73] Assignee: Raymond A. McBrearty, Allentown, Pa.

[21] Appl. No.: 297,224

[22] Filed: Aug. 29, 1994

[51] Int. Cl.$^6$ .............................................. G01B 103/40
[52] U.S. Cl. .................... 364/550; 364/551.01; 340/517; 340/635; 340/825.82
[58] Field of Search .............................. 364/413.02, 550, 364/551.01; 340/517, 635, 641, 825.06, 825.29, 825.72, 825.82

[56] References Cited

U.S. PATENT DOCUMENTS

| | | | |
|---|---|---|---|
| 4,627,860 | 12/1986 | Rowland | 55/162 |
| 5,262,944 | 11/1993 | Weisner et al. | 364/413.02 |
| 5,297,034 | 3/1994 | Weinstein | 364/413.02 |
| 5,307,263 | 4/1994 | Brown | 364/413.02 |

*Primary Examiner*—Ellis B. Ramirez
*Assistant Examiner*—Thomas Peeso

[57] ABSTRACT

The invention provides an inexpensive and electrically isolated remote monitoring apparatus for monitoring the operational status of any oxygen concentrator by specifically monitoring the standard set of high and low pressure diagnostic light emitting diodes provided with most concentrators. Flexible boots enclose the respective optodetectors and are forceably pushed over the diagnostic diodes of the oxygen concentrator so that any light emitted by either diode is detected by the respective optodetector. The optodetectors are further connected to a microcontroller. A telephone line interface port connects to the microcontroller and provides for a telephonic communication link between the microcontroller and a remote computer. When a malfunction is detected and analyzed by the microcontroller, both the type of malfunction and a location code is transmitted to the remote computer.

13 Claims, 2 Drawing Sheets

OXYGEN CONCENTRATOR REMOTE MONITORING APPARATUS

FIELD OF INVENTION

This invention relates to monitoring devices in general, and more particularly to monitoring devices for use with oxygen concentrators.

BACKGROUND OF THE INVENTION

Patients having respiratory and/or pulmonary difficulties have in the past relied upon oxygen tanks for providing their pure oxygen gas requirements. This type of oxygen supply is expensive to maintain and, with the large amount of compressed pure oxygen contained in the supply tank, possesses a potential hazzard for the homeowner. Recently oxygen concentrators have provided an alternate source of oxygen and are increasing replacing the oxygen tank as the primary source of patient oxygen.

An oxygen concentrator utilizies a compressor to pressurize and alternately force atmospheric air through two sieve beds. The sieve beds contain a solid compound which extracts nitrogen from the atmospheric air thereby increasing the oxygen gas concentration in the remaining atmospheric gas thus providing an almost pure flow of oxygen gas to the patient. An electronically controlled valve matrix directs the alternate flow of pressurized atmospheric air into and out of the sieve beds and further controls the delivery of pure oxygen gas to the patient.

The advantages of utilizing oxygen concentrators over conventional tank supplied oxygen are numerous and include lower oxygen delivery cost and the elimination of a large amount of compressed pure oxygen stored in heavy tanks in the home. However, the disadvantages include the occassional malfunction of mechanical components including the compressor and valve matrix and the normally slow deterioration of the sieve beds which eventually decreases the oxygen concentration to an unacceptable level. Sieve bed deterioration is accelerated if a valve malfunction is not timely corrected by the health care provider.

Most oxygen concentrators provide a means of monitoring machine performance which, upon detecting a machine malfunction, activates an audible alarm to alert the patient. The patient must then alert the health care provider of the machine malfunction. This places an additional burden on the patient and family. Further, many oxygen concentrators are not located near the patient because of the noise level of the compressor and therefore an activated alarm may not be heard. Remote monitoring of machine performance would eliminate many of these disadvantages.

Health care providers and manufacturers have both recognized the many advantages of remote monitoring oxygen concentrator performance and a number of patents have been issued in this area. For example, U.S. Pat. No. 4,627,860 issued to Rowland describes an oxygen concentrator which includes a microprocessor and a cooperating means for monitoring the performance of various components of the concentrator. An external apparatus may then be either directly connected or remotely connected through a telephonic communication link to the concentrator to monitor concentrator operation. Although capable of remote monitoring the operation of the concentrator, the external apparatus can only be used with a cooperating concentrator specifically designed to interface with the external apparatus and is not universally adaptable to other concentrators.

Most health care providers must supply the make of oxygen concentrator as stipulated by the attending physician. This forces each health care provider to inventory as many different makes and models as there are manufacturers of oxygen concentrators. For the health care provider to effectively monitor those oxygen concentrators with remote monitoring ability would require a substantial investment in manpower and equipment to receive the different monitoring signals. Additionally, no standard communication protocol exists among the various makes and models which have remote monitoring capability further increasing the cost of this service. Also many popular brands of oxygen concentrators are not equipped for remote monitoring.

While the foregoing prior art have, with varying degrees of success, attempted to provide oxygen concentrators with remote monitoring capability, none of the prior art discloses a universal and programmable monitoring apparatus which can be easily installed on any make of oxygen concentrator. Thus there remains a need in the art for a simple to install, inexpensive and universal oxygen concentrator remote monitoring apparatus.

SUMMARY OF THE INVENTION

The invention provides an inexpensive and electrically isolated remote monitoring apparatus for monitoring the operational status of most oxygen concentrators by specifically monitoring the standard set of high and low pressure diagnostic light emitting diodes provided with these concentrators. These diagnostic diodes are commonly used by the health care provider for routine concentrator maintenance and visually indicate the type of malfunction. The monitoring apparatus comprises two optodetectors enclosed individually within flexible rubber boots which are connected to a microcontroller having a cooperating memory. The flexible boots are forceably pushed over the diagnostic high and low pressure light emitting diodes of the oxygen concentrator so that any light emitted by either diode is detected by the respective optodetector and subsequently sensed by the microcontroller.

The monitoring apparatus also consists of a telephone line interface port which provides telephonic communication between the microcontroller and a remote computer terminal. Further connected to the microcontroller is a battery and low battery detector, a customer ID selector switch matrix and an equipment ID selector switch matrix. The equipment ID selector switch selects the particular make and model of concentrator which is to be monitored by the apparatus and the customer ID selector switch uniquely identifies the patient.

Under normal concentrator operation, the battery operated monitoring apparatus is placed into a low power wait state. Upon detecting any transition in the signals input from the boot enclosed optodetectors, the microcontroller resumes normal operation and inputs the optodetectors signal cadence and compares this information against previously stored cadence information associated with the selected make and model concentrator. The microcontroller then determines the particular malfunction and communicates this information along with the customer ID information through the telephone interface to a remote computer.

It is therefore an object of the invention to provide a programmable monitoring apparatus for remotely monitoring the operational status of oxygen concentrators.

It is another object of the invention to provide a programmable monitoring apparatus for monitoring high and low pressure conditions of oxygen concentrators.

It is still another object of the invention to provide an easily installed programmable monitoring apparatus for oxygen concentrators.

It is yet still another object of the invention to provide an electrically isolated programmable monitoring apparatus for remotely monitoring the operational status of oxygen concentrators.

It is yet another object of the invention to provide a universal monitoring apparatus for remotely monitoring the operational status of any oxygen concentrator equipped with diagnostic light emitting diodes.

BRIEF DESCRIPTION OF THE DRAWINGS

A full understanding of the invention can be gained from the following description of the preferred embodiment when read in conjunction with the accompanying drawings in which.

DESCRIPTION OF THE PREFERRED EMBODIMENT

Figure 1:
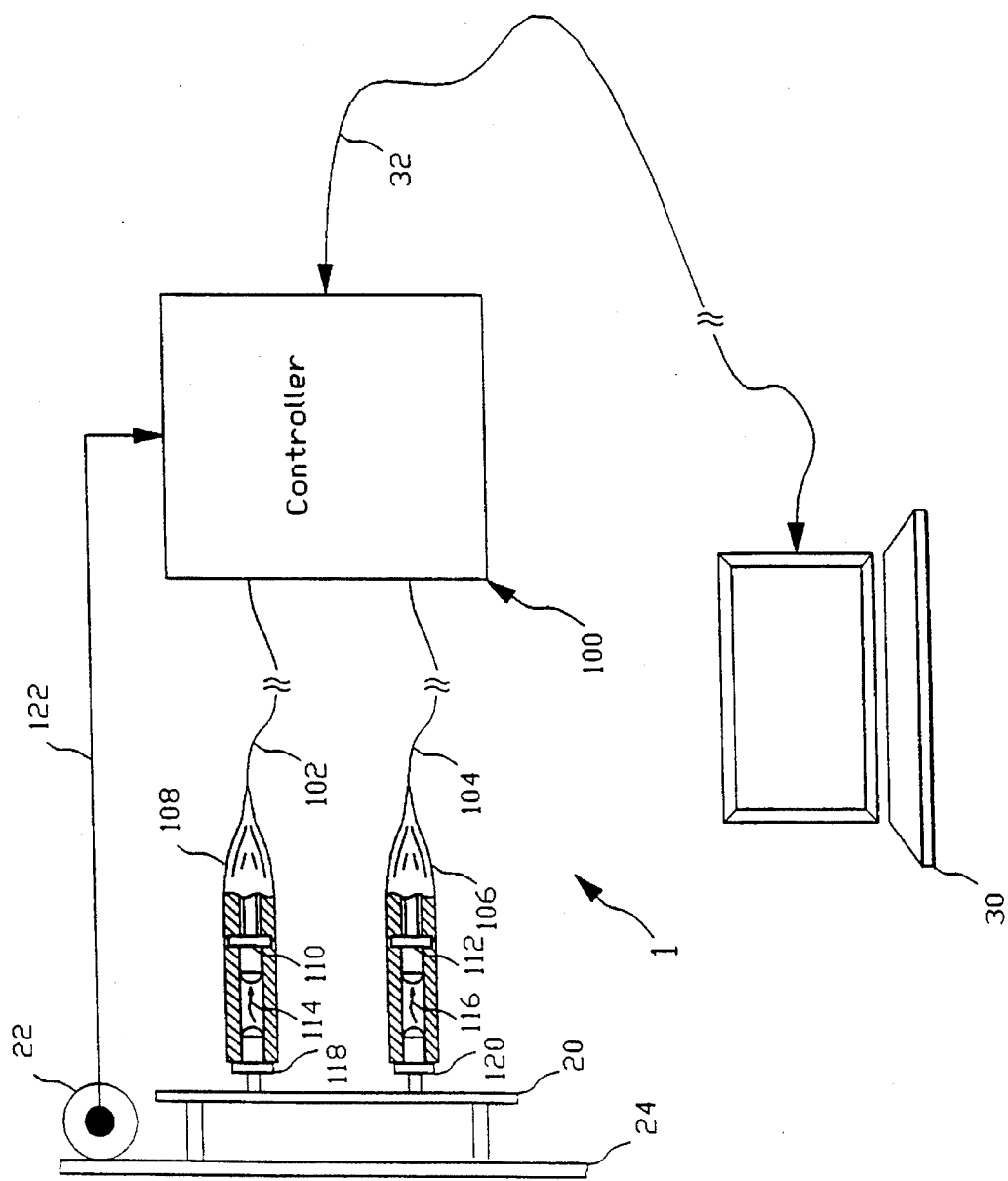
FIG. 1 illustrates an embodiment of the invention attached to diagnostic light emitting diodes of an oxygen concentrator.

Referring now to FIG. 1 of the drawings, there is shown a preferred embodiment 1 of the present invention having controller 100 connected to a birectional communication link 32. The other end of link 32 connects to computer 30. Preferably computer 30 is located at the health care provider place of business. Controller 100 and computer 30 are in bidirectional communication with each other via link 32. In the preferred embodiment, link 32 is a hardwired telephone line. However it is understood that link 32 could also be a wireless link, or could be a combination of a series of wireless and hardwire links.

Further connected to controller 100 is one end of two conductor cable 122. The other end of cable 122 connects to battery 22. Battery 22 is part of the oxygen concentrator and supplies electrical energy to the control and alarm circuits in the event of an AC power interruption. Also connected to controller 100 is two conductor cables 102 and 104. The other end of cable 102 forceably passes through one end of flexible opaque hollow boot 108 and connects to an enclosed conventional two terminal photodetector 110. The opposite end of boot 108 forceably slides over high pressure diagnostic light emitting diode 118. It is therefore understood that boot 108 aligns photodetector 110 with light emitting diode 118 such that light 114 emitted by diode 118 impinges upon photodetector 110. Boot 108 further excludes any ambient light from impinging upon photodetector 110.

Similiarly, the other end of cable 104 forceably passes through one end of flexible opaque hollow boot 106 and connects to an enclosed conventional two terminal photodetector 112. The opposite end of boot 106 forceably slides over diagnostic light emitting diode 120. It is therefore understood that boot 106 also aligns photodetector 112 with light emitting diode 120 such that light 116 emitted by diode 120 impinges upon photodetector 112. Boot 106 also excludes any ambient light from impinging upon photodetector 112. Boots 108 and 106 are preferably molded from a soft pliable rubber.

Diodes 118 and 120 are further mounted to printed circuit board 20 which further attaches to oxygen concentrator panel 24. Printed circuit board 20 contains the circuit and associated electronic components which controls the operation of the oxygen concentrator. Diodes 118 and 120 are illuminated when either respectively a high or low pressure malfunction condition is detected.

Figure 2:
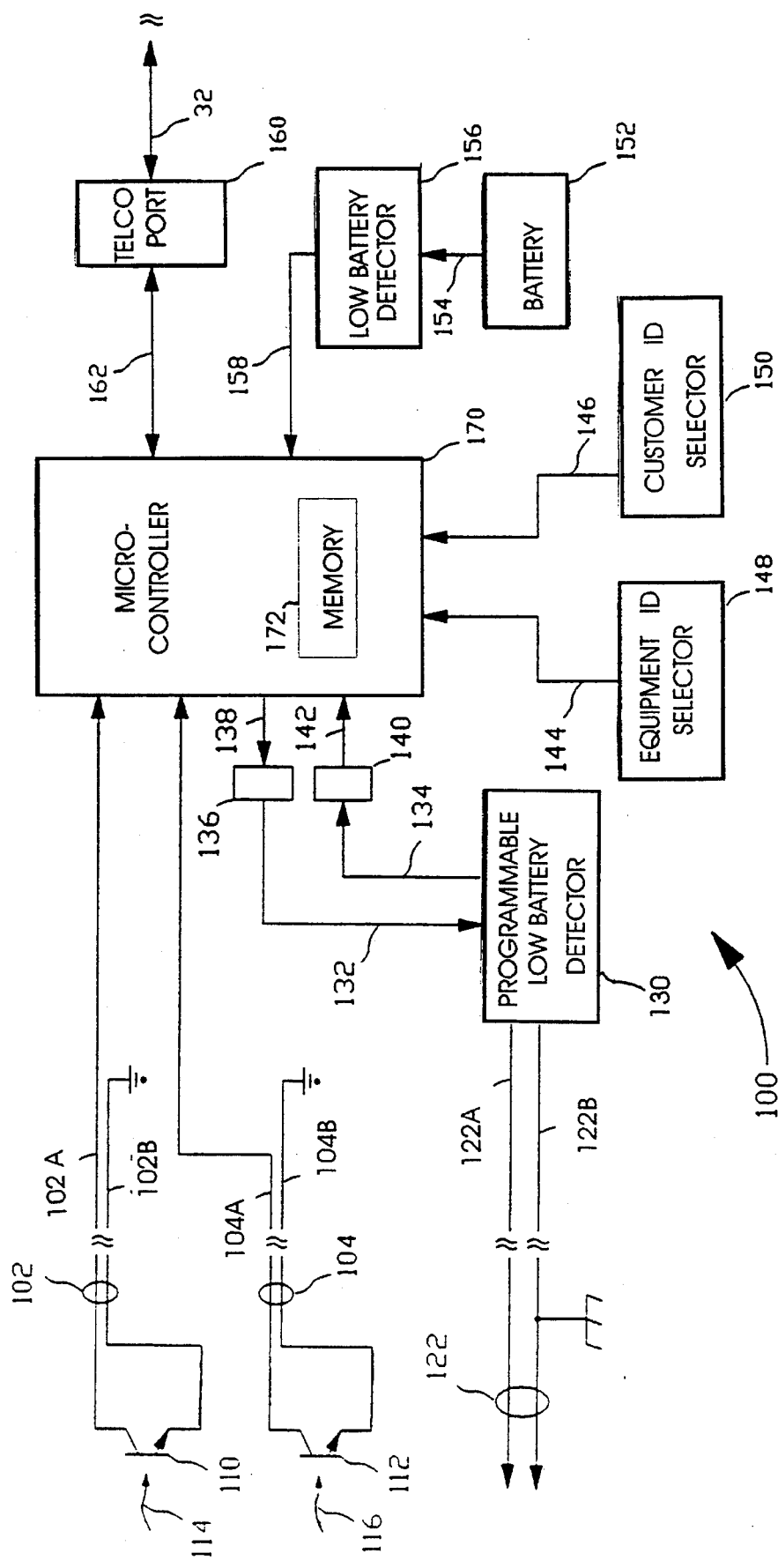
FIG. 2 illustrates a detailed block diagram of an embodiment of the invention.

Referring now additionally to FIG. 2, controller 100 further comprises microcontroller 170 having cooperating memory 172. Microcontroller 170 has further conventional I/O ports with which to input and output signals. Memory 172 further consists of RAM and ROM memory. ROM memory stores program information and the operating parameters associated with all of the possible oxygen concentrators. Further stored in ROM memory is the telephone number of computer 30. RAM memory is used to store temporary data. Microcontroller 170 is preferably a 68HC05 microcontroller manufactured by Motorola Semiconductor.

Connected to microcontroller 170 is bidirectional signal and control bus 162 which connects to conventional telephone company (TELCO) line interface port 160. Telephone link 32 further connects to port 160. Port 160 interfaces microcontroller 170 to, and electrically isolates microcontroller 170 from, link 32 and provides the necessary statutory requirements of Part 68 of the Federal Communication Commission for connecting devices to the public telephone system. Additionally, port 160 in response to micrcontroller 170 initiates connection to telephone link 32, places DTMF dialing tones onto link 32 to dial computer 30, and provides all other necessary functions to establish and maintain a conventional telephonic bidirectional communication link between microcontroller 170 and computer 30.

It is understood that if link 32 is a wireless link, then telephone line interface port 160 would be replaced with a wireless interface port 160 which would then interface microcontroller 170 to wireless link 32. An example of a wireless interface port 160 would include the conventional PCMCIA wireless interface card. Further, if link 32 is a wireless link then remote computer 30 would be adapted to interface with the wireless link 32.

Battery 152 supplies power to microcontroller 170 and further connects to low battery detector 156 via line 154. Battery detector 156 continually monitors battery 152 voltage and places a signal onto line 158 which flows to microcontroller 170 indicating low battery voltage. Battery 152 is preferably two series connected standard 500 milli-ampere-hour AA batteries.

Customer ID selector 150 is a binary switch matrix which the health care provider sets to uniquely identify the patient. Selector 150 sends the patient identification signals onto bus 146 which flows to microcontroller 170.

Equipment ID selector 148 is a binary switch matrix which the health care provider sets to identify the particular make and model of the corresponding oxygen concentrator. Selector 148 sends the equipment identification signals onto bus 144 which flows to microcontroller 170. Microcontroller 170 uses this the ID information placed on line 144 to determine the particular operating parameters associated with the selected oxygen concentrator from the many such sets of operating parameters stored in the ROM part of memory 172.

Programmable low battery detector 130 inputs battery 22 voltage from two conductor cable 122. Conductor 122a connects to the positive battery terminal and conductor 122b connects to the negative battery terminal. Detector 130 is powered from battery 22 and also continually monitors battery 22 voltage. If battery 22 voltage falls below a predetermined threshold voltage, detector 130 places a low battery voltage signal onto line 134 which then flows to conventional optoisolator 140. In response to the signal placed onto line 134, optoisolator 140 then places an electrically isolated equivalent signal onto line 142 which flows to microprocessor 170.

Mircrontroller 170 in response to selector 148 places a threshold voltage select signal onto line 138 which flows to optoisolator 136. In response to the signal placed onto line 138, optoisolator 136 then places an electrically isolated equivalent signal onto line 132 which flows to detector 130. The signal placed onto line 132 programs the threshold voltage of detector 130.

In response to light 114 emitted by diode 118, optodetector 110 places a signal onto conductor 102a with respect to conductor 102b of cable 102 which flows to microcontroller 170. In similar fashion and in response to light 116 emitted by diode 120, optodetector 112 places a signal onto conductor 104a with respect to conductor 104b of cable 104 which flows to microcontroller 170. Thus microcontroller 170 effectively inputs the status of high and low pressure diagnostic diodes 118 and 120.

It is therefore understood that controller 100 is electrically isolated from the oxygen concentrator circuit board 20 by optoisolators 136 and 140, and by optodetectors 110 and 112. Further, controller 100 is electrically isolated from telephone link 32 by port 160.

The health care provider installs preferred embodiment 1 of the invention by first setting equipment ID selector 148 to the proper setting corresponding to the particular make and model of the oxygen concentrator. The provider then sets customer ID selector 150 to a selection uniquely identifying the patient from all other patients whom may be remotely monitored with similarly operating devices. The provider then forceably slides the opened ends of boots 108 and 106 over the respective oxygen concentrator high and low pressure diagnostic diodes 118 and 120. The provider then connects link 32 to interface port 160 and inserts battery 152 powering on the remote monitoring apparatus. The remote monitoring apparatus is now installed and begins operation.

In operation, microcontroller 170 in cooperation with the control program stored in the ROM part of memory 172 first initializes all ports for either input or output operation and then inputs battery 152 status information from line 158. If microcontroller determines that battery 152 has low battery voltage as determined by detector 156, microcontroller 170 initiates a link 32 connection as described more fully below. Otherwise microcontroller 170 continues operation as now further described.

Assuming that battery 152 has sufficient voltage, microcontroller 170 then inputs the customer ID signal from line 146 and the equipment ID signal from line 144. In response to the signal on line 144, microcontroller 170 determines the associated oxygen concentrator operating parameters from a look-up table previosuly stored in the ROM part of memory 172. The operating parameters include the particular threshold voltage with which to program detector 130 and any cadence information associated with diagnostic diodes 118 and 120 necessary for microcontroller 170 to determine the occurrence of a high or low pressure malfunction condition of the monitored oxygen concentrator.

Microcontroller then sends a voltage threshold program signal onto line 138 which is input by optoisolator 136. Optoisolator 136 then outputs an equivalent isolated signal onto line 132 which is input by detector 130. Detector 130 in response to the signal placed onto 132 sets the threshold voltage with which to compare battery 22 voltage input from lines 122a and 122b.

Detector 130 then places a signal onto line 134 if battery 22 voltage is below the programmed threshold voltage. Optoisolator 140 then places an equivalent isolated signal onto line 142. Microcontroller 170 then inputs the signal from line 142 and, if the signal on line 142 indicates that battery 22 voltage is below the programmed threshold, initiates a link 32 connection as described more fully below. Otherwise microcontroller 170 continues operation as now further described.

Microcontroller 170 then inputs signals placed onto lines 102a and 104a and, based upon the retrieved cadence information associated with diagnsotic diodes 118 and 120 for the selected oxygen concentrator, determines the operational status of the monitored oxygen concentrator. If line 102a or 104a signals and their subsequent analysis indicates a high or low pressure malfunction, microcontroller 170 initiates a link 32 connection as described more fully below. Otherwise, microcontroller 170 continues operation as now further described.

With the monitored oxygen concentrator determined to be normally operational, microcontroller 170 then places itself into a low power consumption wait state. In this wait state microcontroller 170 typically draws less than 50 microamperes of current from battery 152. With the preferred two 500 milliampere-hour AA battery 152 installed continued operation in this mode can be expected to exceed one year. Further, in the wait state microcontroller 170 enables any signal transitions occurring on lines 102a, 104a or 142 to immediately cause resumption of normal operation.

Thus, if a previously normally operating oxygen concentrator experiences a valve malfunction which causes a high pressure condition, diagnostic diode 118 illuminates causing light 114 to impinge upon photodetector 110. Photodetector 110 in response to light 114 turns on and places line 102a near ground potential. If a low pressure condition occurred instead of a high pressure condition, diagnostic diode 120 then would illuminate causing light 116 to impinge upon photodetector 112. Photodetector 112 in response to light 116 turns on and places line 104a near ground potential. Additionally, if a low battery 22 voltage is detected a signal is placed onto line 142.

In either case a signal transition on any lines 102a, 104a or 142 causes microcontroller 170 to resume normal operation which then subsequently inputs the cadence information of the signals on lines 102a, 104a and 142. The received signal cadence information is then compared against the previously chosen cadence information corresponding to this particular make and model of oxygen concentrator to determine the type of malfunction which has occurred in the monitored concentrator.

Microcontroller 170, having now determined the type of malfunction, initiates a link 32 connection through port 160 and establishes a telephonic communication link to remote computer 30 using conventional bidirectional telephonic communication protocol. Having successfully established a communication link, microcontroller 170 through port 160 then sends to computer 30 the determined type of malfunction and customer ID information. Computer 30 then transmits back to microcontroller 170 through port 160 the received information. Microcontroller 170 then compares the received to the previously transmitted information and, if an exact match is found, transmits to computer 30 through port 160 a confirmation signal. Computer 30, in response to received confirmation signal, then displays the customer's name, address, and any other pertinent information which the health care provider deems important to be associated with the customer ID information previously sent by microcontroller 170. Additionally, the type of malfunction of the monitored oxygen concentrator is also displayed. The health care provider is therefore immediately notified of both the type and location of the oxygen concentrator malfunction.

It is further understood that the above apparatus could be further extended to those concentrators having diagnostic light emitting diodes monitoring the operation of the valve matrix.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

We claim:

1. A monitoring apparatus for remotely monitoring the operational status of an oxygen concentrator having a plurality of diagnostic light emitting diodes wherein said light emitting diodes indicate the operational status of said oxygen concentrator comprising:

a hollow boot having an opened end for forceably fitting over said light emitting diode;

a photodetector mounted within said boot for detecting light emitted from said light emitting diode;

means responsive to said photodetector for determining the operational status of said oxygen concentrator;

a computer responsive to said determining means for receiving said operational status of said oxygen concentrator.

2. A monitoring apparatus according to claim 1 wherein said determining means comprises:

a microcontroller;

memory cooperating with said microcontroller;

a switch means connected to said microcontroller for selecting from said memory diagnostic cadence information of said diode of said oxygen concentrator.

3. A monitoring apparatus for remotely monitoring the operational status of an oxygen concentrator having a local readout comprising:

means for detecting signals from said local readout;

means responsive to said detecting means for processing said signals to determine said operational status of said concentrator;

means for transmitting information which indicates the status of said concentrator to a remote monitoring terminal.

4. A monitoring apparatus according to claim 3 wherein said transmitting means comprises a wireless transmitter.

5. A monitoring apparatus according to claim 4 wherein said transmitting means comprises a wireless PCMCIA card transmitter.

6. A monitoring apparatus according to claim 3 wherein said transmitting means comprises a telephonic transmitter.

7. A monitoring apparatus for remotely monitoring the operational status of an oxygen concentrator having a plurality of diagnostic light emitting diodes wherein said light emitting diodes indicate the operational status of said oxygen concentrator comprising:

a hollow boot having an opened end for forceably fitting over at least one of said plurality of light emitting diodes;

a photodetector mounted within said boot for detecting light emitted from said one of said plurality of light emitting diodes;

means responsive to said photodetector for determining the operational status of said oxygen concentrator; and a computer responsive to said determining means for receiving said operational status of said oxygen concentrator.

8. A monitoring apparatus according to claim 7 wherein said determining means comprises:

a microcontroller;

memory cooperating with said microcontroller, said memory having diagnostic cadence information of said plurality of light emitting diodes of said oxygen concentrator; and a switch means connected to said microcontroller for selecting from said memory diagnostic cadence information of said one of said plurality of light emitting diodes of said oxygen concentrator.

9. A monitoring apparatus for remotely monitoring the operational status of an oxygen concentrator having a local readout comprising:

optical means for detecting signals from said local readout;

means responsive to said detecting means for processing said signals to determine said operational status of said concentrator; and means for transmitting information which indicates the status of said concentrator to a remote monitoring terminal.

10. A monitoring apparatus according to claim 9 wherein said transmitting means comprises a wireless transmitter.

11. A monitoring apparatus according to claim 10 wherein said transmitting means comprises a wireless PCMCIA card transmitter.

12. A monitoring apparatus according to claim 9 wherein said transmitting means comprises a telephonic transmitter.

13. A monitoring apparatus for remotely monitoring the operational status of a machine having a local readout comprising:

optical means for detecting signals from said local readout;

means responsive to said detecting means for processing said signals to determine said operational status of said concentrator; and means for transmitting information which indicates the status of said machine to a remote monitoring terminal.

* * * * *